(12) United States Patent
Ohlström et al.

(10) Patent No.: US 8,600,684 B2
(45) Date of Patent: Dec. 3, 2013

(54) SPINNER HOME SEQUENCE

(75) Inventors: Agneta Ohlström, Järlåsa (SE); Mårten Bergström, Uppsala (SE); Tobias Söderman, Bälinge (SE); Robert Bielik, Bälinge (SE)

(73) Assignee: Gyros Patent AB, Uppsala (SE)

( * ) Notice: Subject to any disclaimer, the term of this patent is extended or adjusted under 35 U.S.C. 154(b) by 1192 days.

(21) Appl. No.: 11/916,012

(22) PCT Filed: May 31, 2006

(86) PCT No.: PCT/SE2006/050178
§ 371 (c)(1),
(2), (4) Date: May 13, 2008

(87) PCT Pub. No.: WO2006/130111
PCT Pub. Date: Dec. 7, 2006

(65) Prior Publication Data
US 2009/0308470 A1    Dec. 17, 2009

Related U.S. Application Data

(60) Provisional application No. 60/685,535, filed on May 31, 2005.

(30) Foreign Application Priority Data

May 31, 2005    (SE) ....................................... 0501243

(51) Int. Cl.
*F17D 3/00*    (2006.01)
*G01B 11/14*    (2006.01)

(52) U.S. Cl.
USPC ........................................... 702/31; 702/100

(58) Field of Classification Search
USPC ................... 702/31, 46, 49, 100; 250/231.13, 250/231.14, 231.16, 231.17, 231.18, 250/559.41, 559.44; 341/11, 13; 356/43, 356/620
See application file for complete search history.

(56) References Cited

U.S. PATENT DOCUMENTS

| | | | |
|---|---|---|---|
| 6,537,801 | B1 | 3/2003 | Ida et al. |
| 2001/0051714 | A1 | 12/2001 | Chen et al. |

(Continued)

FOREIGN PATENT DOCUMENTS

| | | |
|---|---|---|
| EP | 0 417 305 A1 | 3/1991 |
| EP | 1 195 430 | 4/2002 |

(Continued)

OTHER PUBLICATIONS

International Search Report issued Aug. 30, 2006 during the prosecution of the International Application No. PCT/SE2006/050178.

(Continued)

*Primary Examiner* — Sujoy Kundu

(57) ABSTRACT

The present invention relates to a method for determining the identity of a microfluidic device and a home position by means of a set of home position marks on the microfluidic device, which is of the type used in a microfluidic system. Said method comprises following phases: a microfluidic device scanning phase, wherein a microfluidic device is scanned for mark identifiers; a microfluidic device identifying phase, wherein at least one a characteristic feature of the set of home marks is/are determined and used for identifying the identity of the microfluidic device; a home position determining phase, wherein the home position is determined by the use of at least a subset of the home position marks identified during said previous phases. The present invention relates to a set of home marks, a microfluidic device carrying such a set of home marks, a microfluidic system, a computer program product and a computer program on a computer usable medium.

30 Claims, 7 Drawing Sheets

(56) References Cited

U.S. PATENT DOCUMENTS

| | | |
|---|---|---|
| 2002/0145960 A1 | 10/2002 | Worthington et al. ..... 369/47.48 |
| 2003/0231312 A1* | 12/2003 | Sjoberg et al. ................ 356/401 |
| 2005/0202733 A1* | 9/2005 | Yoshimura et al. ........... 439/839 |

FOREIGN PATENT DOCUMENTS

| | | |
|---|---|---|
| JP | 2005-257337 | 9/2005 |
| WO | WO-0216037 | 2/2002 |
| WO | WO-03035538 | 5/2003 |
| WO | WO-03082730 | 10/2003 |
| WO | WO-03087779 | 10/2003 |
| WO | WO 2004/025559 | 3/2004 |

OTHER PUBLICATIONS

Extended European Search Report issued in European Application No. 06748018.6, mailed Sep. 24, 2010.

Office Action issued in Japanese Application No. 2008-514601, mailed Sep. 6, 2011.

* cited by examiner

SPINNER HOME SEQUENCE

TECHNICAL FIELD

The present invention relates to an identifying method of microfluidic devices used in microfluidic systems.

More specifically, the present invention relates to sets of home position marks, a microfluidic device carrying such a set of home position marks, a method for determining the identity of a microfluidic device and determining the home position by means of a set of home position marks on a microfluidic device of a type used in a microfluidic system. The present invention also relates to a microfluidic system, a computer program product and a computer program on a computer usable medium.

BACKGROUND OF THE INVENTION

The term "microfluidic" refers to a system or device having one or a network of chambers and/or channels, which have micro scale dimensions, e.g., having at least one cross sectional dimension in the range from about 0.1 µm to about 500 µm. The term "microfluidic" in the context of device, system, disc etc refers to the fact that liquid volumes in the µl-range are transported within the system. This means that there may or may not be liquid transport within a certain part of the system, for instance the microfluidic device/disc. The µl-range includes the nl-range as well as the picolitre range. Microfluidic substrates are often fabricated using photolithography, wet chemical etching, injection-molding, embossing, and other techniques similar to those employed in the semiconductor industry. The resulting devices can be used to perform a variety of sophisticated chemical and biological analytical techniques.

Microfluidic analytical systems have a number of advantages over conventional chemical or physical laboratory techniques. For example, microfluidic systems are particularly well adapted for analyzing small sample sizes, typically making use of samples on the order of nanolitre and even picolitre. The channel defining substrates may be produced at relatively low cost, and the channels can be arranged to perform numerous analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures.

Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

The microfluidics technologies/devices are capable of controlling and transferring tiny quantities of liquids to allow biological assays to be integrated and accomplished on a small scale.

Microfluidics is the miniaturization of biological separation and assay techniques to such a degree that multiple "experiments" can be accomplished on a "chip" small enough to fit in the palm of your hand. Tiny quantities of solvent, sample, and reagents are steered through narrow channels on the chip, where they are mixed and analyzed by such techniques as electrophoresis, fluorescence detection, immunoassay, or indeed almost any classical laboratory method.

Today a number of products varying in many respects are available. Laboratory chips may be made from plastic, glass, quartz or even silicon. The fluid may be driven by centrifugal forces, mechanical pressure or vacuum pumps, by inertia, or by one of several electrical methods; fluid flow can be diverted around the chip by mechanical valves, surface tension, voltage gradients, or even electromagnetic forces.

In the technique of using centrifugal forces to drive the fluid a disc that can be spun is used. Some discs have been of the same physical format as conventional CDs. Samples are placed near the center of the disc and centrifugal forces, created as the disc rotates, push them out through channels cut into the plastic, circumventing the need to design sophisticated electrokinetic or mechanical pumping structures.

As will become evident in the forth-coming description the present invention is in particular applicable to (but not limited to) micro-analysis systems that are based on micro-channels formed in a rotatable, usually plastic, disc, often called a "lab on a chip". Such discs can be used to perform analysis and separation on small quantities of fluids.

In order to reduce costs, it is desirable that discs are not limited for use with just one type of reagent or fluid, but should be able to work with a variety of fluids. However, scientists, laboratory staff, etc in a laboratory handles a lot of different chemical samples. To be able to perform and run different chemical tests for a various number of samples, the operators of the microfluidic system will have to handle a great number of different microfluidic devices. A common problem is to identify a certain microfluidic device, e.g. within a series of identical microfluidic devices used within a series of experiments.

Said identification problem may be solved in different ways, e.g. by using different kind of labels attached to the microfluidic device structure. One kind of labels store identity information in an electronic memory chip. The chip is readable, but may also be writable and/or erasable. To get access to the memory chip content for reading, writing, or erasing purposes such means, equipment and program software have to be added to the analysis system instrument. All extra equipment and program software increase the total cost for the system and also the system instrument. The adding of an electronic label to the microfluidic device adds an extra cost to the total cost and increases the manufacturing complexity of the microfluidic device. Suggested solutions of the identification problem are therefore not considered to be satisfactory from an economical point of view.

Furthermore, it is often desirable during the preparation of samples that the disc permits the user to dispense accurate volumes of any desired combination of fluids or samples without modifying the disc. A microanalysis device for fluids provided in a rotatable disc is described e.g. in WO-01/46465. A liquid transfer station has a robot that transfer at least one sample or any other predetermined liquid aliquot at a time from the sample and reagent station to a microfluidic device, for instance in the form of a disc that can be spun. The station has means for transfer of liquid samples, and other liquids, for instance a number of injection needles connected to syringe pumps or a number of solid pins may be used for the transfer of samples. Said needles and pins may be configured in different numbers of rows and columns having different distance between the tips in both directions. Another alternative is the microdispensor described in WO 9701085.

The needles or pins have to be exactly maneuvered to an appropriate inlet of each channel. The microfluidic devices, e.g. microfluidic discs, may be designed in different ways and each microfluidic device differs individually due to the manufacturing process. A home position mark is preferably placed in an outer circumferential zone outside the detection areas or in some other position, which can be detected with high accuracy. The position coordinates of each specific spot of the surface of the disc is given as the angular position relative to the home position mark and as the radial position relative to the circumference or axis of symmetry or relative to any other arbitrary fixed position on the device. The process or method for finding the home position mark and determining is called for "Homing the device (disc)" and the "Homing" process. Known homing processes involves the scanning of the disc for finding an edge of the home position mark.

In WO 03087779 there is described a known homing process. This process involves a check if a mark is a home position mark or not. One home position mark on a rotating disc placed on a disc holder of a microfluidic instrument is detected by a home position mark detector when a home mark is passing. Said known method comprises following phases:

a disc scanning phase, wherein a disc is scanned for mark edges;

a home mark identifying phase, wherein the false home marks are rejected and the correct home phase is identified;

a home position determining phase, wherein the home position is determined by use of the exactly determined edges of the home position mark.

Said method has increased the possibility to locate the exact home position. However, some times the detected edge is a false edge of a home position mark. If a defect or pollution is present in the close vicinity of an edge of a home position mark, said defect or pollution may influence the determination of the exact location of the home position. Even a very small deviation from the true home position may ruin a whole experiment run as the injection needles are not placed properly in the inlets of the micro-channels. At occurrence of home position displacement, the aliquots and wash-liquids will be dispensed and wasted on the surface of microfluidic device.

Another problem with the use of only one home position mark is that the microfluidic device may be discarded if one of the edges of the home position mark is a defect edge. The instrument system will not be able to identify the home mark and the microfluidic device will be rejected by the system.

Another problem with the known home position mark is that the home position detector is capable of detecting the home position mark even though the microfluidic device is placed up-side down. The instrument system will not react for this kind of fatal mistake resulting in warning or alarm and/or a stop of the experiment run as the home position mark is locatable. All aliquots and wash-liquids will be dispensed and wasted on the surface of the bottom of the microfluidic device.

BRIEF DESCRIPTION OF THE INVENTION

It is an object of the present invention to present a new solution of said identification problem and to increase accuracy of a home position by means of a set of home position marks on a special microfluidic device type.

Said object is achieved by the claimed method for determining the identity of a microfluidic device and determining the home position by means of a set of home position marks on a microfluidic device according to the independent claim 1, a set of home marks according to the independent claim 22 and a microfluidic device carrying such a set of home marks according to the independent claim 29.

The present invention also relates to a microfluidic system according to independent claim 16, a computer program product according to independent claim 11 and a computer program on a computer usable medium according to claim 12.

Different aspects and variants of the invention are defined by the dependent claims.

One advantage with the present invention is that the system will work faster and more properly, even though a lot of false marks are present on the device that would have normally disturbed the homing process.

Another advantage is that the yield will increase as less microfluidic devices have to be discarded.

Further one advantage is that the microfluidic system will be capable of detecting and warning if the microfluidic device is turned up-side down when inserted in the analysis system instrument.

Another advantage is that the present invention provides possibility to give different microfluidic devices a unique detectable identity.

DETAILED DESCRIPTION OF THE INVENTION

The present invention relates to microfluidic systems.

Different microfluidic systems are known. One type of systems comprises a controller unit and a microfluidic instrument. Such a system is called a Stand Alone System. Each system has its own data and operates completely stand alone. The interaction with the system may be performed at an associated Personal Computer (PC).

Another system can be considered as a group of instruments plus a common persistent storage location, e.g. database. Many instruments can operate on the same set of data (Method Data, Microfluidic Device Data, etc). All interaction with the system needs to be performed at an instrument connected computer, a controller. This second system is often called a Distributed Database Solution.

In a third solution, the distributed solution, the system is considered as a group of instruments, a common storage persistent storage location (database), and a number of clients. With this solution the same functionality as in the above-mentioned Distributed Database Solution is reached. In addition there will be a possibility to interact with the system from non instrument connected computers. Examples of additional provided functionality are:

Remote monitoring of instruments.
Perform functions that are not instrument specific (Method Development, Evaluation of processed data, etc.

With this third solution it is possible to control (Start, Pause, Abort) the processing remotely, that is, from a non instrument connected computer.

An operator/user can control and monitor the performance of the microfluidic instrument from the controller. The microfluidic instrument comprises of a number of different stations, each station being capable of performing one or a number of defined operations. Different types of microfluidic instruments consist of different kinds of stations or number of stations. Therefore, some operations will not be provided for or applicable on a certain type of microfluidic instrument.

The operations are initiated from the controller.

Figure 1:
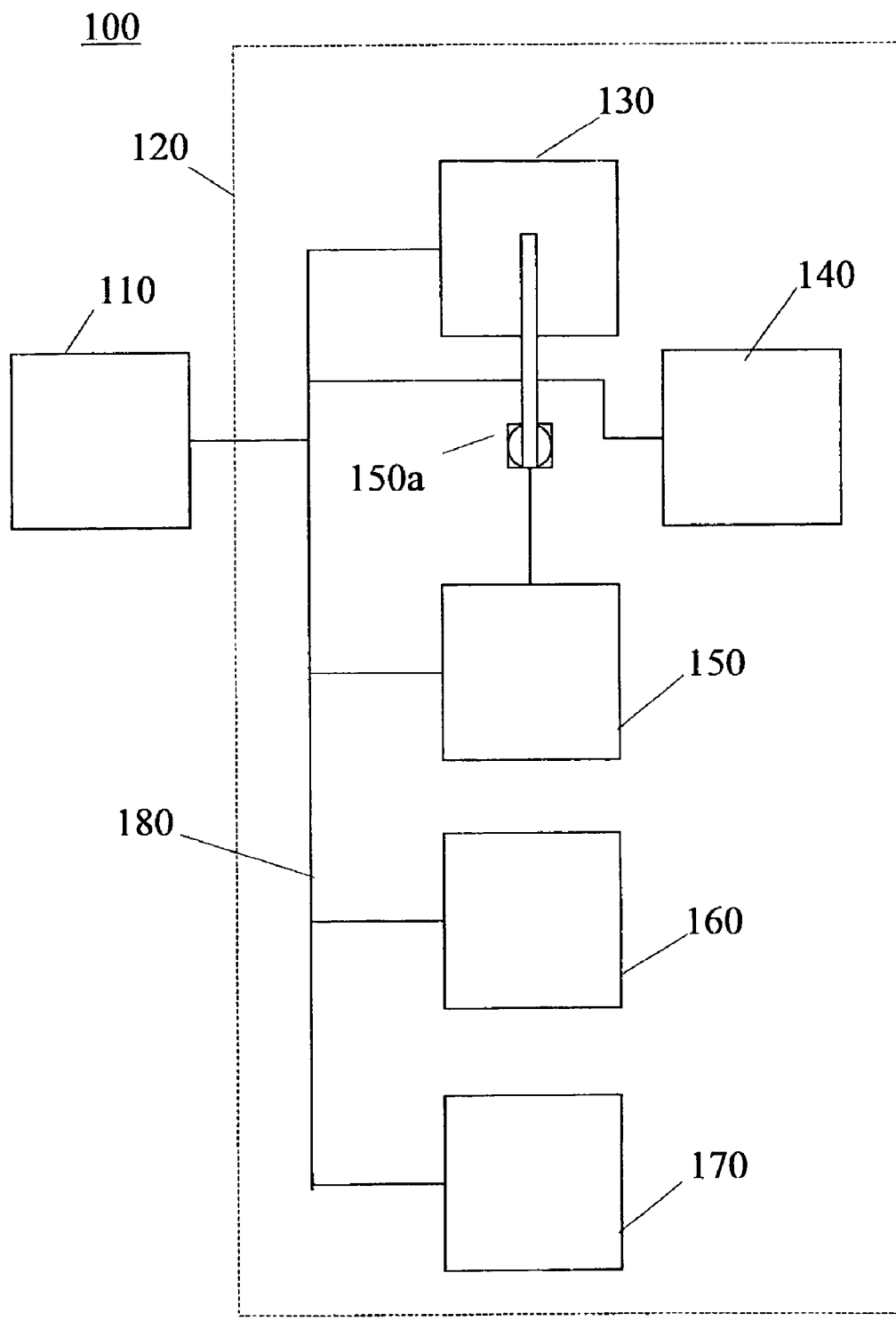
FIG. 1 is a block diagram depicting schematically a microfluidic system.

FIG. 1 is a block diagram depicting schematically an embodiment of a microfluidic system 100 that includes a control unit, also denoted controller, 110 and an instrument 120 comprising a sample and reagent station 130, a wash station 140, a liquid transfer station 150, at least one station 160 for implementing transport of liquid within the microfluidic device e.g., a spinner station and a detector station 170. The controller 110 may comprise one or more computers outside the instrument and/or one or more central processors within the instrument. The controller is connected to the instrument 120 and its different stations via a conductor or data bus 180 and operation orders are transmitted either as electrical or optical signals or included in a suitable predetermined protocol to hardware circuits distributed between the stations.

A controller may comprise different control means, for instance electronic and programmable control means with operator's interface and software, not further disclosed, may be assigned to the detector arrangement among others for a) recognizing one or more pairs of start/stop-positions (angular and/or radial) for irradiating if the detection principle utilized requires irradiation and/or for collecting radiation,
b) identifying individual sub areas in detection areas or elsewhere in the surface of the disc,
c) controlling the simultaneous rotating of the disc and the incremental radial displacement of a detector head,
d) collecting radiation data from the detection areas/detection microcavities,
e) treatment and presentation of the collected data, and/or
f) determining the time at which a particular angular position is in front of the objective of the detector head from the rotational speed.

Different parts of the arrangement may communicate with the controller 110. The controller will in the preferred variants instruct the detector head to successively collect radiation from distinct and pre-selected parts of the surface of the disc. Typically the controller is programmed to start collecting radiation at a position, primarily an angular and/or a radial position, which is prior to an intended detection area, and to end the collecting at a position, which is after the same detection area. Preferably the starting position and the ending position are at essentially the same radial distance. This means that the sub-areas from which radiation is collected primarily are located within detection areas. Yet further, in preferred variants, sub-areas close to the detection areas are also included. If the radiation requires that the substance is irradiated, which is the case if fluorescence is measured, the control means also defines the settings for the start and stop positions for irradiation. These latter settings are typically essentially the same as for collecting radiation.

The start and stop signals for collecting radiation is preferably directly linked to the angular positions in the disc at which collection is to start and end, respectively. This also includes that due account is taken for delays that may be inherent in the system or preset, i.e., the start and stop signals may have to be initiated before the focal area is positioned in front of the start and stop position, respectively. If an angular aligning system within the microfluidic system comprises an encoder, the encoder signals corresponding to a start position and a stop position are used to define the time period during which radiation is to be collected. In an alternative, the start and stop for collecting radiation is linked to a preset rotating speed, i.e., the controller calculates from a preset rotating speed the time at which the start and stop position should be in front of the objective.

The controller may be programmed to change the radial position of the detector head (focal area) after a predetermined number of revolutions of the disc, for instance after 1, 2 or more revolutions with preference for 1.

Further, the present system have a sample and reagent station 130 comprising means for storing samples, reagents or other liquids. Said samples, reagents or other liquids is stored in some kind of container, such as a micro plate or multiwell plate, a test tube rack or a test tube. Said plate is designed as a matrix of small containers or wells. Said plate can have different sizes depending on the number of wells. The container may be loosely fixed at a container holder, for instance a so called carousel, which is a circular revolving plate.

The liquid transfer station 150 has a robot 150a that transfer at least one sample or any other predetermined liquid aliquot at a time from the sample and reagent station 130 to a microfluidic device, for instance in the form of a disc that can be spun. The station have means for transfer of liquid samples, and other liquids, for instance a number of injection needles connected to syringe pumps or a number of solid pins may be used for the transfer of samples. Said needles and pins may be configured in different numbers of rows and columns having different distance between the tips in both directions. Another alternative is the microdispensor described in WO 9701085.

Said needles and pins may or may not be washed in a wash solution between the transfers of samples and reagents. Washing is done by means placed in a wash station 140.

The liquids dispensed to a microfluidic device are transported within the device by means associated with the station 160 for implementing liquid transport. This station may be a spinner station in case the microfluidic device is adapted to permit liquid transport caused by spinning. The result of a process carried out within the microfluidic device is determined by means for detecting (a detector) which is located in a detector station 170.

The arrangement of the detector station 170 is adapted for measuring radiation from a plurality of detection areas each of which is associated with a detection microcavity in a microfluidic. The arrangement comprises:

(a) a detector head with a focal area, and a disc holder which are linked to a means enabling for the detector head, i.e., the focal area to transverse, the surface of the disc when the disc is placed in the disc holder.
(b) an angular aligning system for recognizing the angular position of the part area which at a particular time is covered by the focal area, and
(c) an optional radial aligning system for recognizing the radial position of the part area which at a particular time is covered by the focal area, and (d) a controller, e.g., computer with software, which controls
   (i) equipment causing the focal area to transverse the detection areas in an annular zone of the disc, and
   (ii) the detector head successively collects radiation in a pre-selected manner from individual sub areas of essentially the same size as the focal area within at least one of the detection areas in said annular zone.

As shown in FIG. 1, each of said stations are connected to the controller 110 and controlled and monitored from the controller 110 by means of a number of operations. A software operation is defined as a logical group of hardware instructions, which are performed to accomplish a certain function, such as:

Implementing transport of liquid, for instance spinning the device if the device is in the form of a disc that can be spun in order to induce liquid flow.

Sample transfer to a specific common distribution channel or a specific microstructure.

Reagent transfer to a specific common distribution channel or a specific microstructure.

Position the microfluidic device.

Incubate the liquids at a certain position in the microstructures for a specific time.

Detection, i.e. detection of the results of the method carried out in the microfluidic device.

An operation may consist of a number of steps. A step is a non-dividable instruction, such as a ramp in a spin operation. A set can be constituted by putting together a number of these operations in a desired order. Such a set is defined as a method and controls all parts conducted within the instrument. It prescribes a type of microfluidic device and defines a set of actions, operations. It may prescribe halting for conducting steps outside the instrument, for instance incubations at constant temperature when the method concerns cell culturing.

The present invention relates to a method for determining a home position by means of a home position mark on a special microfluidic device type used in a microfluidic system, as described above.

Figure 2:
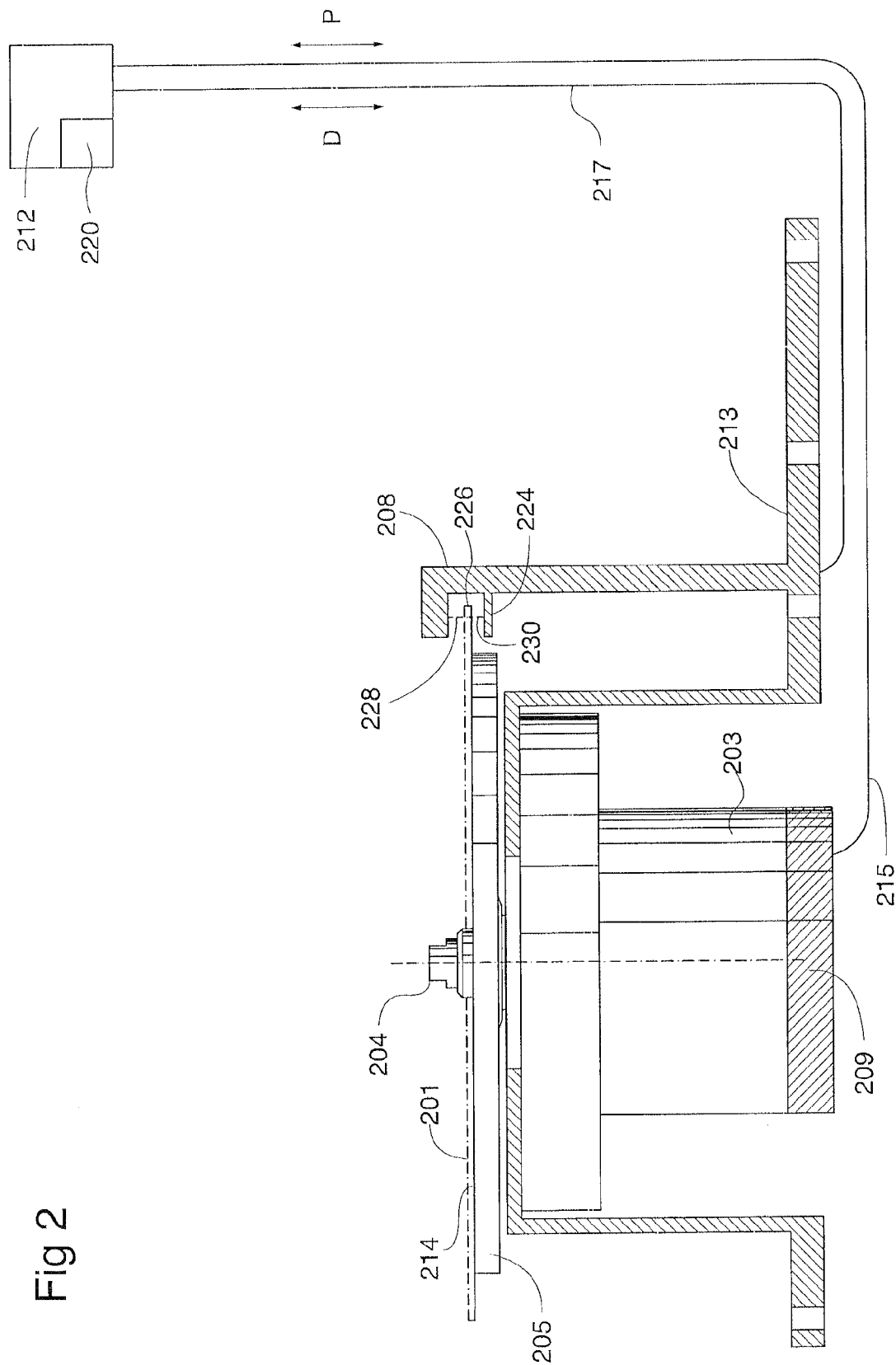
FIG. 2 shows a home position mark detector arrangement in a microfluidic system.

FIG. 2 shows a home position mark detector arranged with station where a microfluidic device is rotated, e.g. at a spinner station or detector station, in a microfluidic system. In a typical variant, a motor 203 (e.g., a spinner) with a rotatable shaft 204 carrying a disc holder 205 are supported on a frame structure 213. The motor 203 is controlled by the controller and is able to rotate the microfluidic device in both spinning direction and the rotating speed that can be varied, e.g., within an interval between 0-15,000 rpm, such as above 60 rpm. The rotation of the disc 201 may be stepwise. The disc holder 205 is preferably a plate on which the disc can be placed. The disc holder could also be a device that holds the disc at its periphery. In order to reduce wobbling of the disc (if the disc is skewed), the side 214 of the plate facing the disc may comprise a system of evenly distributed uncovered shallow grooves or channel openings that are connected to a vacuum system by which the disc can be sucked to the plate. See for instance WO 03025549 and WO 03024596 which are incorporated herein by reference.

The system also has to contain a position device 209 for determining when a predetermined angular position of the disc is in front of a needle or an detector objective of the system. Different position devices are known in the market, such as encoders, absolute position encoders etc. A simple but less accurate alternative is to include calculating means that calculates the time needed from a preset rotation speed and the angular distance between the predetermined position and a home position mark (i.e., from the preset rotation speed and the angular position co-ordinate). This kind of calculating means may be associated with the controller.

An absolute encoder is a position device that progressively gives the angular distance from the home position while the disc is rotating.

The position device 209 is typically associated with the motor 203, the shaft 204, and the disc holder 205 and it is connected to a position controlling means of the controller. By associating the position device directly with the disc 201 it is likely that the most accurate determination will be accomplished. The position device typically divides each revolution of the shaft into a large number of grades, denoted as resolution grades, for instance >5 000, such as >10 000 or >20 000 or >30 000. The position device should be able to give the angular position coordinate for the part of the disc which is in front of a home position mark detector with an accuracy and resolution of ±1°, such as within ±0.1° or within ±0.01° (provided there are 360° per revolution). The exact accuracy needed will depend on the size of the disc, radial position of the detection area, the required sensitivity, size of detection area, etc The position controlling means 220 of the controller 212 will receive or transmit different data using a position signal P over the connection 215 depending on the type of position device 209. If the position device is an encoder generating a pulse for each resolution grade, the position controlling means involves a pulse counter for registering the pulse sum value that is representing the current position of the disc relative to a start position or the home position, and the detector. If the position device is an absolute encoder, the position controlling means will receive or transmit an absolute measure of the angular distance from a start position or the home position. In either case, the position controlling means of the controller is able to control the position device. The position controlling means sets a desired position and transfer the desired value to the position device, which receives the position and controls the motor 203, the shaft 204, and the disc holder 205 to set the disc in the desired position.

On each microfluidic disc 201 are a set of home position marks (310a, 310b, . . . in FIG. 3) preferably placed in an outer circumferential zone outside the detection areas or in some other position. The home position marks must have at least one characteristic feature that is detectable, preferably with high accuracy, and possible to identify for the controller and the microfluidic system. Such a characteristic feature may be the angular length of the mark, denoted $L_{mark}$. The position coordinates of each specific spot of the surface of the disc are given as the angular position relative to the home position and as the radial position relative to the circumference or axis of symmetry or relative to any other arbitrary fixed position on the disc.

A home position mark detector 208 typically has a fixed position outside the disc, for instance on the frame structure 213. A home position mark detector 208 is capable of detecting when a set of home position marks (305 in FIG. 3) is passing. A home position mark detector may also be movable, if necessary.

In the embodiment illustrated in FIG. 2, the home position mark detector 208 comprises an electromagnetic beam source 222 and a transducer arrangement 224. The outer circumference of the disc is placed in the gap 226 between two optical fibres, the source fibre 228 and the detector fibre 230. One of the fibres, denoted as the source fibre 228, is situated on the same side of the disc as the electromagnetic beam source. Said source fibre conducts the electromagnetic beam from the source and illuminates a spot of the disc's passing circumference on which the home marks are situated. On the other side of the disc the beams cut-through area is bigger than the cut-through area of the fibre. However, the receiving end of the detector fibre will only receive a well-defined part of the scattered beam. The detector fibre 230 conducts the beam to a transducer arrangement 224 that registers/measures the intensity of the received electromagnetic beam. The transducer arrangement 224 may comprise a electromagnetic transducer and a comparing means. The electromagnetic transducer generates an electric intensity signal including information in relation to the incoming beam intensity. The intensity signal may be a DC signal, of which the output voltage level is depending on the intensity of the incoming beam. The comparing means receives the electric intensity signal from the transducer. The comparing means will compare the intensity information, for instance the output voltage with a threshold value. The comparing means may be designed to provide a "high-level" output signal, e.g. "1" or 5 Volts, when the output voltage exceeds the threshold value, and a "low-level" output signal, for instance "0" or 0 Volt, when the intensity signal is below the threshold value. The level of the threshold value may be adjustable for setting the sensitivity of the detector. The home position mark detector provides an output signal, the detector signal D, to the controller. The output signal of the comparing means may be connected over a conductor 217 to the controller directly or via an interface input/output circuit to the controller. The controller is able to register the changes between the high and low levels, and when they occur in time.

The comparing means may alternatively be included in the controller instead of the transducer arrangement.

Depending on the sensitivity of the detector, everything causing enough influence on the intensity of the beam is possible to register. When scanning the outer circumferential zone of the disc for the set of home position marks, depending on the pre-set sensitivity, both the set of home position marks and other marks caused by defects in this zone will be registered. Such defects can be dirt fixed on the disc or defects related to a manufacturing problem of the disc. The set of home position marks is made during the process of manufacturing the microfluidic disc. Different types of home marks are possible to use. For a microfluidic disc that is injection molded, it is convenient to form the home position marks at the same time as the channel pattern before the lid is fixed on top of the disc base. The home marks may be formed as a grid pattern comprising parallel ducts and ribs laying in a perpendicular direction relatively the rotation direction. When the beam hits within the area of the home position mark, it will be scattered and the beam intensity left after passing the area will be low. However, the quality of each home mark is depending on the prevailing conditions during the manufacture. Therefore, the sharpness of the borders and beam reducing features may vary from disc to disc.

When a mark—a home position mark or a false mark—is passing the beam, the beam intensity received by the transducer will be reduced. In the case the mark and its border is distinct, the beam intensity changes instantly from high to lower, i.e. low, level when the first leading edge of the mark border meets the beam. The received beam intensity will be low until the second, trailing edge of the border passes the beam and the beam intensity changes from low to high. In the case that the border of a mark is un-sharp, the change from high to low intensity will be extended in time as the intensity will decrease as the incoming beam intensity is fading. The detected position of the edge will depend on the sensitivity and the pre-set detector arrangement threshold value.

In a more general sense, a home position mark of a microfluidic device is an area on the device which is distinguishable from areas of the device surrounding the home position mark by a home position mark detector associated with the instrument in which the device is processed. The area corresponding to a home position mark area thus comprises measurable physical or chemical characteristics of a size and/or a kind that are not present in, the surrounding areas of the device (or vice versa). A home position mark and its identifiers, e.g. the edges, are determined by the detector used and its settings. For instance if the microfluidic device has a mark of some kind that can not be detected by the detector for the home position mark that mark is not a home position mark and there are thus no identifiers to be detected. In the case the detector for instance is based on measuring light absorbance or light transmittance through the device and the device has a local area which is thinner and/or comprises a light absorbing material and therefore detectable by the detector then the local area can be used as a home position mark and detected borders between material of different characteristics may be used as identifiers (edges). In the case the transfer between the different material are stepwise (e.g. two three or more steps) the extent of the home position mark can be defined by the settings of the detector and computer used. For instance the settings can be selected so that the detector and the system regard the area between any two steps in change as the home position mark and the change in material at these particular steps then defines identifiers. Similarly also applies to other detectable characteristics of identifiers that locally can be incorporated into or on the surface of microfluidic devices, for instance magnetism, fluorescence, chemiluminescence, radioactivity, reflectivity, light scattering, electrical conductivity etc. In preferred home position marks the changes in the characteristics used are typically abrupt and/or only alternate between yes or no situations or vice versa.

The home position detector 208 may detect and react for every trailing edge and/or leading edge of each mark. The detector generates a level change in the detector signal from high to low every time an edge of a mark is detected. The controller receiving the detector signal registers the level change and stores the pulse sum value from a pulse counter means of the controller as a position value/data in a column of a table in a memory connected to the controller. Each pulse sum during the first lap corresponds to a unique position on the disc. Hence, a pulse sum corresponds to a position in a defined direction from the start position. That is an angular distance in a defined direction from the start position $n_p=0$. A certain angular distance is equivalent to the angle of an arc unit multiplied with a certain number of pulses, the pulse sum value $n_p$.

Figure 3:
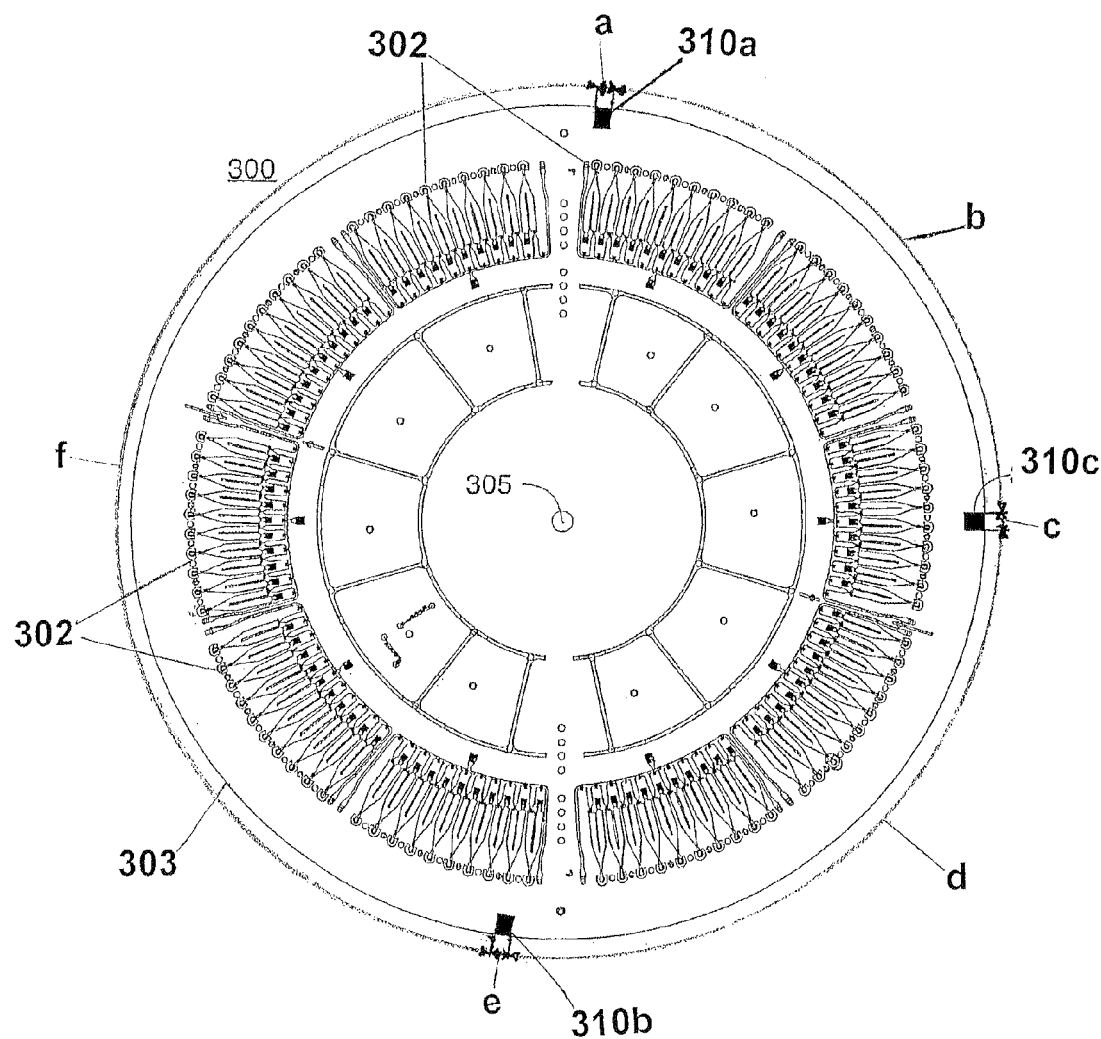
FIG. 3 is a schematic picture of a microfluidic device in form of a disc comprising a set of home position marks according to the invention.

FIG. 3 is a schematic picture of a microfluidic disc 300. A rotatable disc is earlier described e.g. in WO-01/46465. The microfluidic device may be made from different materials, such as plastics, glass, silicone polymers, etc. The detector area should be transparent/translucent for the detection principle utilized by the detector. The disc has a central recess 305 for a disc holder and a disc edge 303 defining the outer border of the outer circumference area. As described above and in referenced prior art documents, samples may be placed near the center of the disc and centrifugal forces, created as the disc rotates, may push them out through channels cut into the plastic, circumventing the need to design sophisticated electrokinetic or mechanical pumping structures.

The microfluidic device 300 used in the various aspects of the invention comprises a plurality of microchannel structures 302 in which aliquots of liquids are transported and/or processed. The microfluidic device may also comprise common channels connecting different microchannel structures, for instance common distribution channels for introduction of liquids and common waste channels including waste reservoirs. Common channels including their various parts such as inlet ports, outlet ports, vents, etc., are considered part of each of the microchannel structures they are connecting. Common microchannels may also connect fluidly groups of microchannel structures that are in different planes. The terms "microchannel", "microconduit", etc., contemplate that a channel structure comprises one or more cavities and/or channels/conduits that have a cross-sectional dimension that is ≤$10^3$ μm, preferably ≤$10^2$ μm. The lower limit is typically significantly larger than the size of the largest reagents and constituents of aliquots that are to pass through a microchannel. The volumes of microcavities/microchambers are typically in the nl-range, such as ≤1000 nl or ≤500 nl or ≤100 nl or ≤50 nl or ≤25 nl, which in particular applies to the detection microcavities. Chambers/cavities directly connected to inlet ports for liquids may be considerably larger, e.g., microchambers/microcavities intended for application of sample and/or washing liquids may thus be in the W-range, such as ≤100 μl or ≤50 μl or ≤20 μl, including also the nl-range. Microformat means that one, two, three or more liquid aliquots that are transported within the device have a volume in the μl-range, i.e., ≤1000 μl such as ≤100 μl or ≤50 μl including but not limited to the nl-range (nanoformat), such as ≤1000 nl or ≤500 nl or ≤100 nl or ≤50 nl. The controller of the microfluidic system has to be able to control and manoeuvre aforementioned needles, pins or detector head to said small cavities with an accuracy of a few μm. The controller has to have the exact position data for different inlet ports, outlet ports, vents, detection positions, etc., of each disc type using the correct home position. Said position data may be stored and possible for the controller to retrieve from the storage, alternatively, the controller may be programmed to calculate the position data. It is therefore very important to find the correct home position mark and to determine the accurate home position on the disc.

The device comprises at least two home position marks defining a set of home position marks designed to indicate a detectable positive spinning direction, i.e. at least detectable by the home position mark detector arranged with the spinner station in the microfluidic system instrument; see FIG. 2. When the motor 203, controlled by the controller, is spinning the disc holder in what is predefined as a positive direction, the controller is able to detect by means of the home position mark detector whether the set of marks is spun in the positive direction, i.e. the set of marks is passing the mark detector in the order indicating that the device is spun in the positive direction, or in the opposite direction. When the set of marks is passing the mark detector in the order indicating that the device is spun in the opposite direction although the disc holder is spun in the positive direction, the system controller is programmed to stop the spinning and indicate to an operator of the system that the microfluidic device is turned upside down. For each kind of microfluidic device and device in a series, the set is unique.

The amount of designs of the marks in a set to indicate the spinning direction is considered to be unlimited. When designing a set of marks, it is possible to vary different features of a set of marks, e.g. the number of marks within a set of home position marks, the angular length of each mark, the depth of each mark, the distance between different marks, etc. The amount of variable features provides possibility to code different characteristics of a microfluidic device. For instance, the set of home marks provides a possibility to identify a certain microfluidic device within a series of identical microfluidic devices used within a series of experiments, a possibility that will be most appreciated by the operators, such as scientists, laboratory staff, etc.

In the following, it will be discussed a number of different embodiments of the invention. Even though the number of suggested embodiment designs is limited, said number should only be considered as examples of the inventive idea and not a limitation of the scope of the invention.

For indication of a spinning direction according to the invention not more than two home position marks are necessary. The system controller will be able to detect the spinning direction by detecting in which order the two marks pass the mark detector. They may for instance be individually different.

Figure 3A:
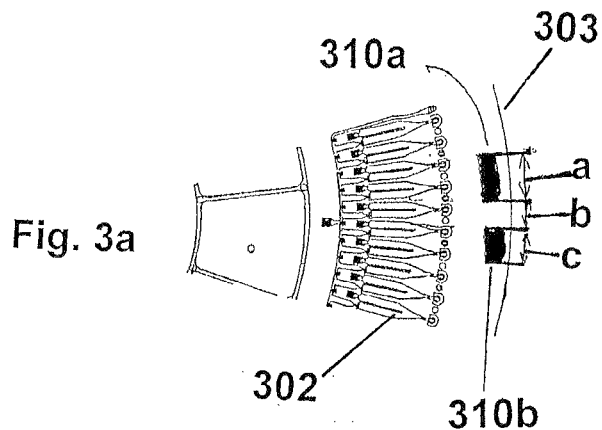
FIGS. 3a, 3b and 3c schematic picture of a part of a microfluidic device in form of a disc comprising a set of home position marks according to the invention.

In FIG. 3a, a set of home position marks 310a, 310b is showed. In this embodiment, the set is located in the periphery of the microfluidic device 300. For indication of the positive spinning direction, the set of home position marks consists of one leading mark 310a and one trailing mark 310b. The leading home position mark 310a may have at least one unique detectable feature distinguishing the leading home position mark from each of the other marks of the set. The leading home position mark 310a does not need to be the first home position mark in a set of home position marks, however, the leading mark needs to have at least one home position mark trailing the leading mark when the microfluidic disc is spinning/rotating in the positive direction. The trailing home position mark 310b may have a detectable feature distinguishing the trailing home position mark from the leading home position mark. The angular length of each mark is a characteristic feature that is possible to change from one disc to another disc in the manufacturing process of the disc or microfluidic device. In this example, the angular length of the leading mark is indicated a, the trailing mark has the angular length c and the angular distance between the two marks is indicated b. Any angular length or distance is defined in resolution grades. It is therefore important to calibrate the instrument, microfluidic device and the detector to the actual used resolution grade scale for avoiding measuring failures and mistakes. After the scanning procedure and the identification procedure, which procedures will be described in more detail in the following, it's possible to identify the home position marks by comparing the result of said procedures with data stored in a home position mark identification table provided as digital information together with other program software by the microfluidic device provider. It is possible to identify a special microfluidic device by comparing the measured and calculated angular length a, b, and c with the corresponding characteristic features a*, b* and c* stored in the home position mark identification table. The table involves the necessary data information to identify which of the marks that is the leading mark and which of the marks that is the trailing mark and thereby determining the positive direction. Each of the characteristic features a, b, or c or any combination of said two or three determined feature values may be used for identifying a special disc in a series of discs. The table may also inform which of the located mark identifiers, in this embodiment the edges, that should be used for determining the exact home position (home location), see FIG. 6.

According to one embodiment, each home position mark has a detectable leading identifier, in this case an edge, and a detectable trailing identifier, e.g. edge, and the exact home position may be situated somewhere in the area from the position of the leading edge of the first mark of the set of home position marks, e.g. the leading mark 310a, to the position of the last home position mark, e.g. trailing edge of the trailing mark 310b, the positions of said edges incorporated in said area. However, the exact home position may likewise be situated somewhere outside the area from the position of leading edge of the first mark of the set of home position marks, e.g. the leading mark, to the position of the last home position mark, e.g. trailing edge of the trailing mark, the positions of said edges incorporated in said area.

Figure 3B:
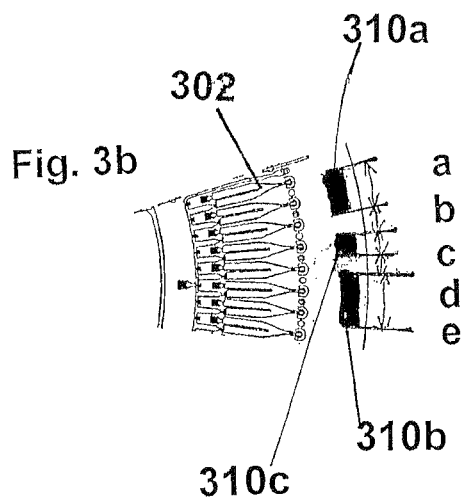

In FIG. 3b is another configuration of a set of home position marks illustrated. Said set consists of three marks 310a, 310c and 310c. When the device is rotating in positive direction, the first mark 310a is the mark having an angular length indicated a, the second mark 310c in the middle has the angular length indicated c and the last mark 310b has the angular length indicated e. Between the first mark 310a and second mark 310c is an angular distance indicated b and between the second mark 310c and third mark 310b is an angular distance indicated d. The angular lengths and distances a-e are all characteristic features that could be changed and used for identification of a special disc/device or special features of a disc in an identification table. The more special disc features that a disc provider wants to involve in the identification table for a microfluidic disc, the number of home position marks may be increased.

FIG. 3 illustrates a preferred embodiment of a configuration of a set of home position marks. The set of home position marks consists of three marks 310a, 310b and 310c as in the example illustrated in FIG. 3b. The home position marks are more spread along the outer circumference surface of the disc than in the example illustrated in FIG. 3b. In this preferred embodiment, the angular distances a, c and e of the three marks are the same, i.e. a=c=e. Further, the angular distance between the third mark 310b and the first mark 310a is defined as the characteristic feature distance f. The angular distances b, d and f are possible to change and use as characteristic features for identifying one disc from another, i.e. different discs have different sets of the angular distances b, d and f. It is advisable to avoid that the marks are symmetrically distributed around the circumference of the disc, b=d=f, as such a distribution could jeopardise the identification of the home position.

Figure 3C:
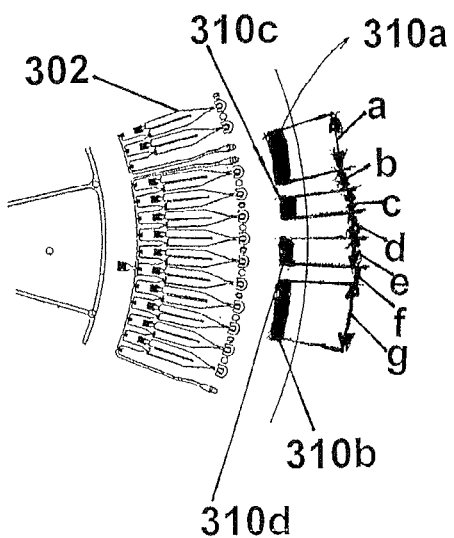

In FIG. 3c, the set of home marks consist of four home position marks, but even more home position marks may be used in a set.

Figure 4:
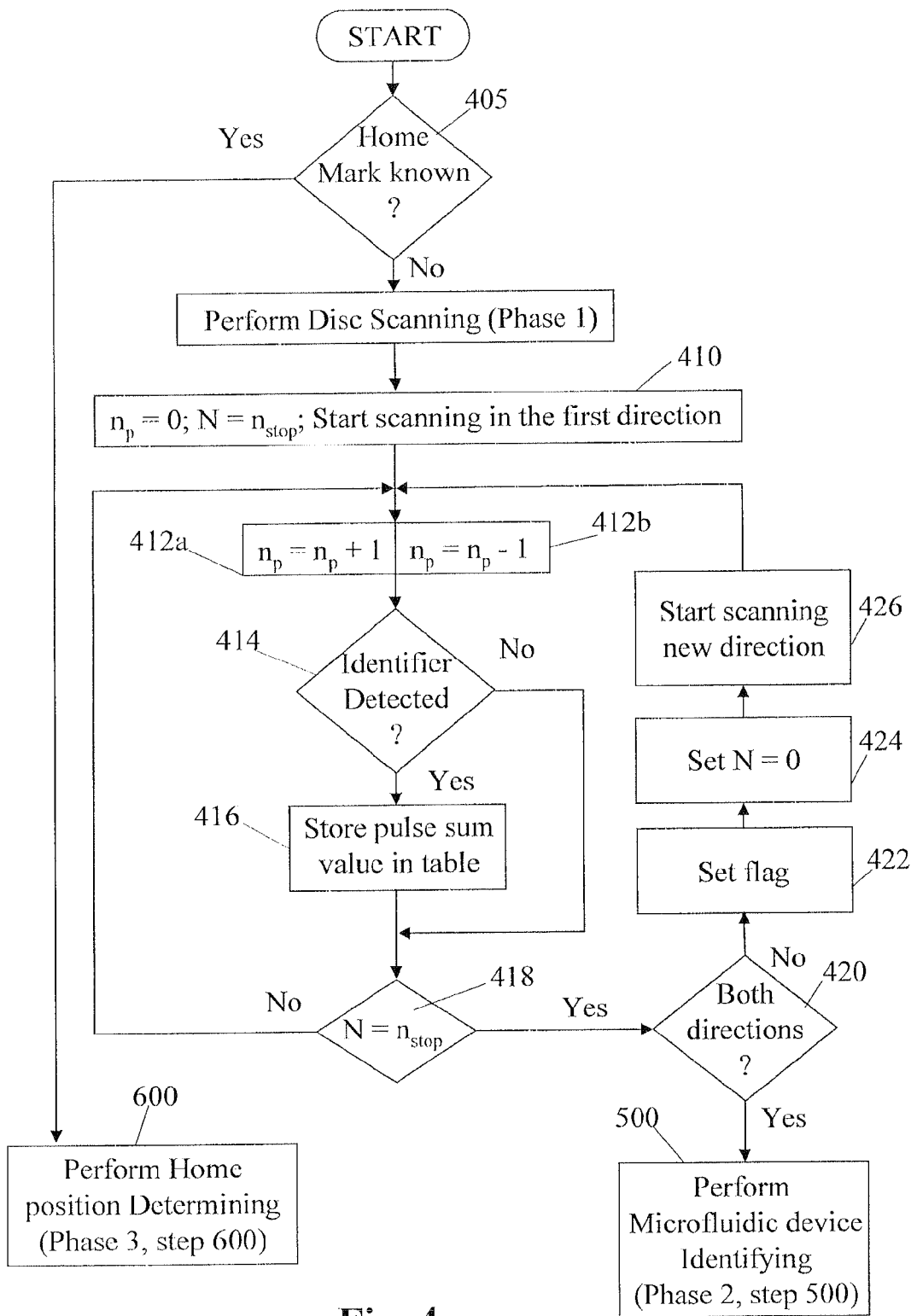
FIGS. 4-6 are flowcharts illustrating an embodiment of the present invented method.
Figure 5:
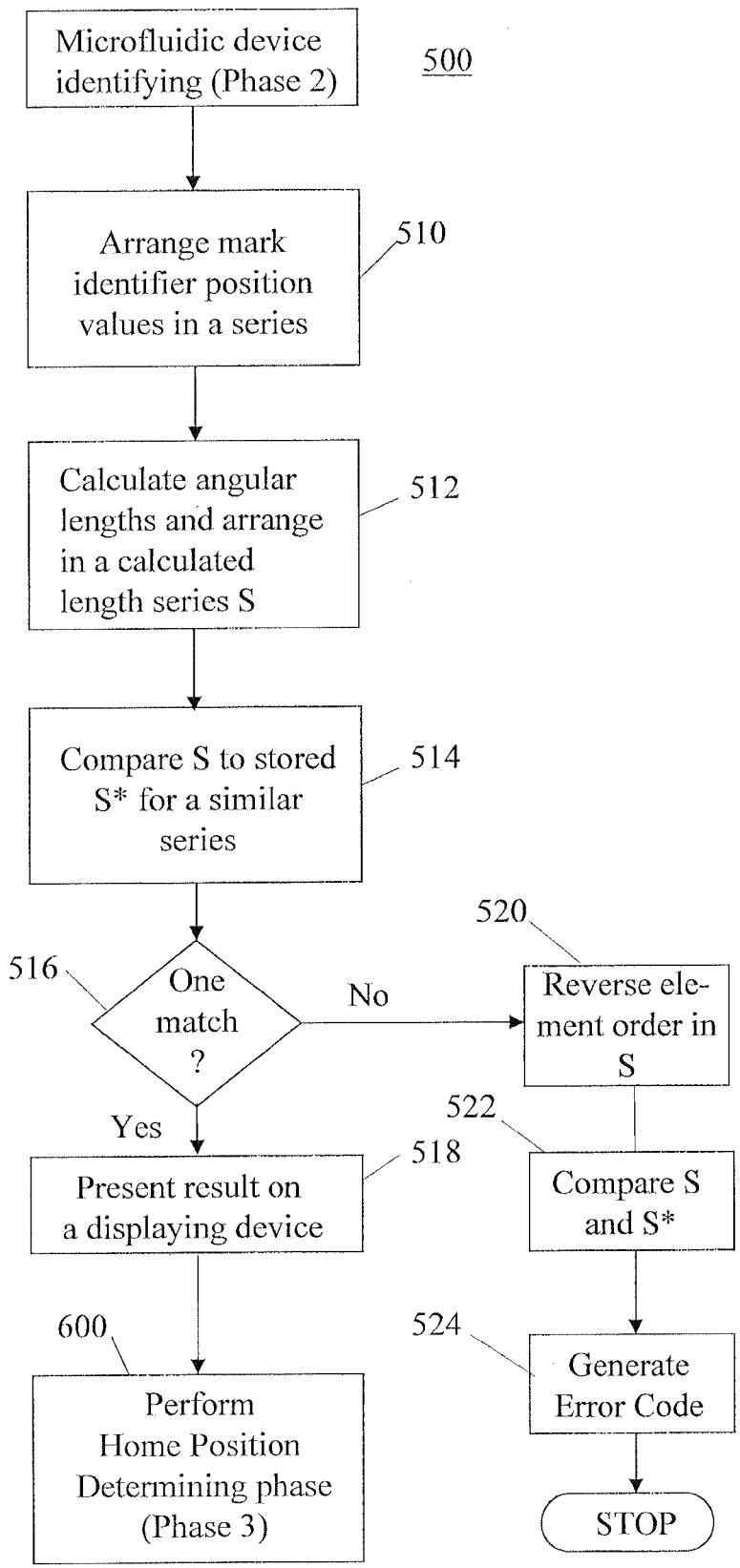
Figure 6:
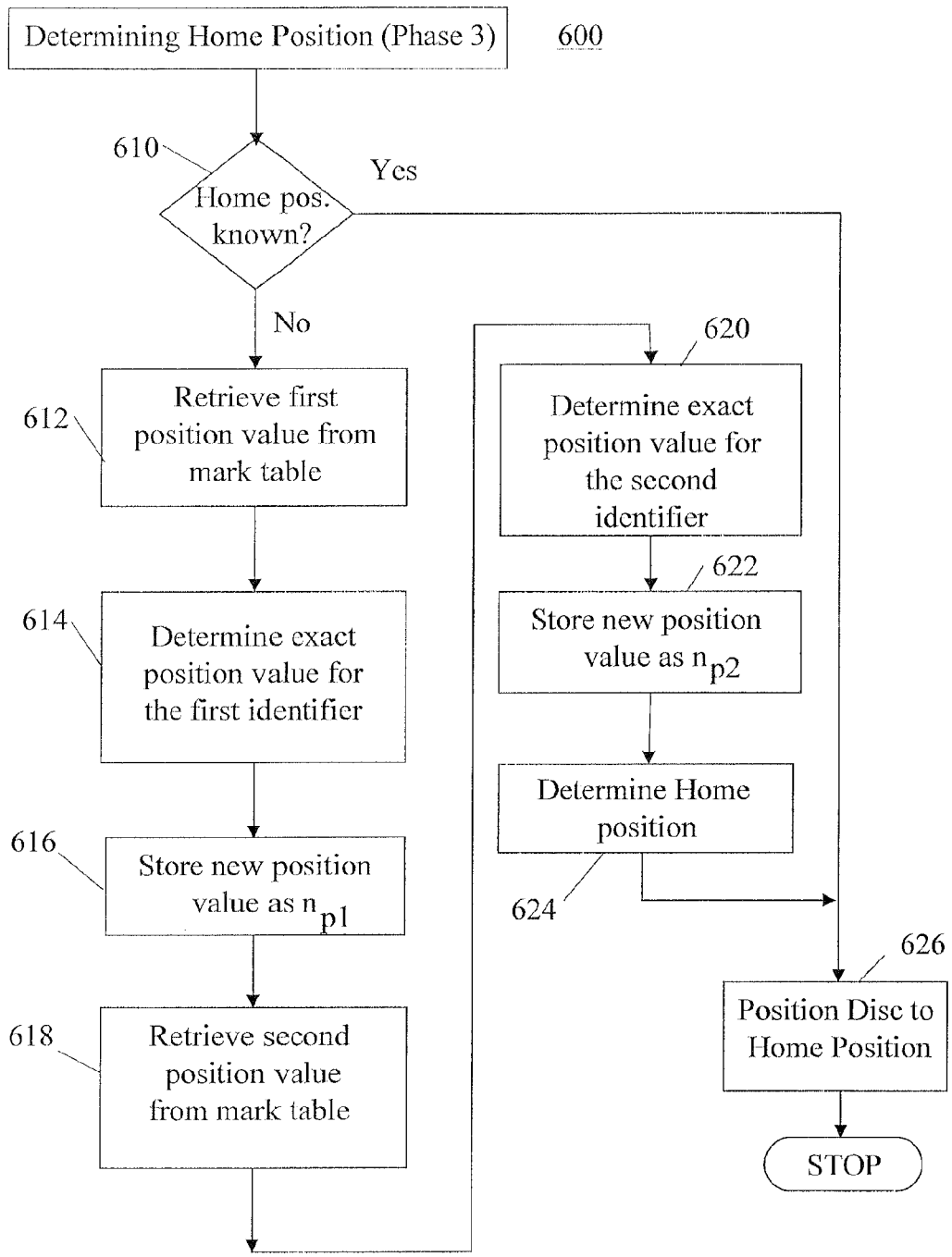

The present invention provides a method for identifying a microfluidic device and finding the correct home position marks and determining the accurate home position on the current device laying on a device holder. The current process is often denoted as the "homing process". FIGS. 4-6 are flowcharts illustrating an embodiment of the invented method.

In this embodiment of the invented method the detector will detect and react for every trailing identifier of a mark. In another embodiment of the invented method, the detector is set to detect the leading identifier of each mark. In the present embodiment the detector generates a change in a detector signal, e.g. a level change from high to low every time a trailing identifier of a mark is detected. Vice versa is also possible defining other embodiments of the invention. The controller receiving the detector signal registers the change and stores the position data stored in the position controlling means of the controller as a position value/data in a column of a table in a memory connected to the controller. Each pulse sum during the first lap correspond to a unique position on the disc. Hence, the position data corresponds to a position in a defined direction from the start position. That is an angular distance in a defined direction from the start position $n_p=0$. A certain angular distance is equivalent to the angle of a resolution grade multiplied with a certain number of pulses, the pulse sum value $n_p$.

To each microfluidic disc belongs a corresponding disc program software which is loadable from any suitable memory device into the microfluidic system controller (described above). Said disc program software comprises data and information about the set of home position marks, e.g. the number of home position marks, their angular length, angular distance between the closest identifiers, e.g. edges of two different marks etc. Said disc program software is preferably prepared by the microfluidic disc manufacturer and provided together with the disc. In this way it's possible to give each microfluidic disc/device a unique identification by variating different detectable disc/device features, such as mark angular length, number of marks, mark distance etc.

When the first phase 400 of the invented process of finding the home position starts, the controller tests, in step 405, if the home position is already known due to the fact that the process has been run for the current microfluidic disc. If the home position and the home position mark of the current disc has been determined, the test is positive, yes, and the method continues with step 600, wherein the process continues with phase 3, determining the home position (see FIG. 6). If the process has not been run for the current disc, the test is negative, no, and the homing process starts with the first phase, the disc scanning. In step 410, a reset signal is generated by the controller to the pulse counter that receives said signal on its reset input and the pulse sum $n_p$ is set to "0" (zero), the stop position N is set to a maximum pulse sum $n_{stop}$ corresponding to a stop position that is preferably located somewhere on the second revolution or lap, and the disc is started to spin in the first direction. A scanning revolution or lap last for more than a single revolution of the disc. The stop value is therefore chosen to be greater than the number of pulses corresponding to exactly one lap. During the disc rotation, a new pulse is generated by the aforementioned encoder for every resolution grade and unit of angular sector movement that a resolution grade represents. The pulse is added to the pulse sum value of the pulse counter in the position controlling means, as in step 412a, if the disc rotates in a first direction, but subtracted from the pulse sum value, as in step 412b, if the disc rotates in a second direction.

In step 414, when a trailing identifier has been detected, the controller registers a change in the detector signal from the home position detector and the controller stores, step 416, the number of pulses corresponding to the position on the disc relatively the start position in a column of a mark table. A first column is filled row by row from the top and downwards. The number of rows filled with a position value corresponds to the number of mark identifiers along the arc that the beam scans during the scanning procedure. The last position value in the first column belongs to a mark that will provide the first position value in the opposite direction during the second half of the scanning phase. Therefore, the second column will be filled row by row from the bottom and upwards, as the position values in this column is received during the opposite rotation direction. The last row in the first column is the bottom of the whole table and the first position value of the second lap will be put in the last row. The positions of identifiers of the same mark will therefore be linked in a correct way.

The scanning procedure will iteratively search all arc unit sectors (an arc unit sector corresponds to the angular distance of a resolution grade) for new trailing identifiers. In step 418, the sum $n_p$ is compared to the stop value N that corresponds to the stop position. Therefore, the disc will rotate a predetermined scanning distance, for an example 10% of a lap, further beyond said start position until the stop criteria in step 418 is fulfilled, yes, and the disc rotation stops.

The next moment of the scanning process is to scan the disc in the opposite direction to find the other identifier(s) of each mark that was registered during the first scanning lap. Therefore, the method continues testing if the disc already has been rotated in both directions before starting the disc rotation in the opposite direction. Such a test is performed in step 420. A flag in a special memory address indicates that both directions has been scanned. Said test in step 420 occurs when a scanning lap is finished. If the flag is absent, only one direction is finished and a second lap has to be scanned.

The flag is set, step 422, the stop value N is set to zero, step 424, and the second scanning in the other direction starts as the controller initiates the motor to rotate the disc in the other direction, step 426. The stop criteria is set to zero, because the disc rotates in the opposite direction and the pulse counter of the position controller means will therefore count down from the maximum value to zero. Thus, the pulse counter counts down and for each arc unit sector scanned the pulse sum is decreased with one unit, step 412b. As soon as a trailing identifier is detected in an arc unit sector, a characteristic change, such as a level change, is detected in the detector signal by the controller and the pulse sum of the pulse counter is read and stored in the table, step 416. The scanning process proceeds until the counter pulse sum fulfils the stop criteria, yes, step 418. As soon as the pulse sum $n_p$ is zero the central processor stops the rotation and scanning. The beam lands exactly on the original start spot on the disc. The disc has been rotated in both directions, and as the flag was set when the second scanning lap started, the flag indicates that both directions has been scanned and the criteria in step 420 is fulfilled (yes). The second phase of the process, which is to identify the set of home position marks and the microfluidic device, can start, step 500 in FIG. 5.

In FIG. 5 the algorithm of the process of identifying the microfluidic device, denoted as the second phase, 500, is illustrated. The second phase starts with step 510, in which the processing unit reads all the stored identifier position values, row by row in the mark table and arranges them in an identifier series in the order as the identifiers are located in the set on the microfluidic device and passes the home position detector when the device is spun in the positive direction. In the next step, step 512, the controller calculates the angular lengths, i.e. the characteristic features that are used in this example, between each one of two adjacent identifiers and arranges the calculated angular lengths in a calculated length series S=[a, b, c, d . . . ] according to their individual location in the set. In step 514, the series of different lengths and distances S=[a, b, c, d, . . . ] is compared to a number of stored different series $S^*=\{S^*_n\}$ of angular lengths and distances, $S^*_n=[a^*, b^*, c^*, d^*, \ldots]$ wherein n=1, 2, 3, . . . , stored in the home position mark identification table.

In step 516, if S doesn't match any $S^*_n$, the series is false (no) and a direction checking phase starts. The controller is programmed to check, in this phase, if the marks of a set of home position marks have been scanned in the wrong order when scanned in a pre-determined positive direction. Said check starts in step 520 and turns the order of the elements of the calculated length series S over, i.e. changing places of the first element ((a), the angular length of the first home position mark and the last element, changing place of the second element from the beginning of the series with the second element from the end of the series, and so on until the order of elements in a series S is reversed defining a new series $S_{-1}$ (e.g. a series S=[a,b,c,d,e,f](see FIG. 3) will become $S_{-1}$=[f, e,d,c,b,a] after the order reversing is finished). In the next step 522, the series $S_{-1}$ is compared to the same stored different series $S^*_n$ as in step 514, described above.

If a match $S_-=S^*_n$ is detected in step 522, a special error code, or special error message, is generated and presented, in step 524, for the system operator on an operator display. Said code/message informs that the microfluidic device is turned upside down, and has to be turned over. When the microfluidic device has been turned to the correct position, i.e. the upper side is directed upwards, the process is started from step 400, phase 1, again.

If no match is detected in step 522, an error code/message is generated and presented, in step 524, for the system operator on said operator display. That means that current disc is not acceptable and it is no use to continue the homing process. The disc may be discarded or a new disc scanning phase, phase 1, may be performed. Especially when more than one hit are detected in step 516, a new disc scanning phase, phase 1, may be relevant to perform.

If instead the condition in step 516 is true, yes, which occur when the series S matches one of the stored series S*, the microfluidic device is identified and the homing process can continue with step 600 (see FIG. 6). Data about the microfluidic device may be read from the home position mark identification table and displayed, step 518, on a display screen or other device connected to the analytical system instrument.

The third phase of the preferred embodiment of the present invention will now be described in more detail in association with FIG. 6. This phase of the process determines the exact position of the home location.

The home position may be defined anywhere on, between or outside two detected identifier position values of a set the home marks. As an example and embodiment of the present invention, the home position is defined to be located somewhere between two pre-selected identifier position values.

As the invented method makes use of a number of home position marks for identification and spinning direction purposes, a number of marks and mark identifiers, e.g. edges, are available for use when determining the home position. The home position can be defined to be located in the middle between two pre-selected identifier positions. The identifiers are pre-selected by the microfluidic device manufacturer and it is not necessary that said pre-selected identifiers belong to the same mark. For each microfluidic device, the home position mark identification table states which of the number of mark identifiers that are selected for home position determination and which formula the controller has to use when calculating the home position.

The first step of the method 600, is to check, in step 610, if the method for finding the home position already has been used for the present microfluidic disc and if there already exists a exact home position. This could be done if a flag is set in a certain storage address every time the present method has been run. An alternative test is to check if there is a position value present. If a flag is present or a home position value is present (the home position parameter has a value greater than zero), the condition in step 610 is fulfilled, yes, and method will proceed to step 626, in which the disc is positioned in the home position.

If the condition is not fulfilled, no, the method retrieves from the mark table the first position value corresponding to one of the two pre-selected home position identifiers, step 612. The controller will determine exact position value for this first identifier, step 614, by only scanning the area surrounding the retrieved position slower than during the first phase of the method. A new threshold value increasing the methods sensitivity might be set by the controller and used in the detector, however, this could be optional. The new position value $n_{p1}$ is stored to be used in the home position formula, step 616.

The controller retrieves the second position value from the mark table, step 618. The controller will determine exact position value for this second identifier, step 620, by only scanning the area surrounding the retrieved position slower than during the first phase of the method. A new threshold value increasing the methods sensitivity might be set by the controller and used in the detector, however, this could be optional. The new second position value $n_{p2}$ is stored to be used in the home position formula, step 622.

The two identifiers of the home mark position are now known. In step 624, these position values is used for calculating the home position, or origin, for the local coordinate system of that microfluidic disc. The home position may be defined anywhere on the outer circumferential zone of the disc, but preferably the home position is placed on or between the two position values of the set of home marks. As an example and embodiment of the present invention, the home position can be defined, to be located in the middle between the home mark position values. E.g., the home position $N_{home}$ may be calculated by use of the formula $$N_{home} = \frac{n_{p1} + n_{p2}}{2}. \quad (1)$$

Finally, when the home position is known, the disc is rotated so the beam of the home position detector hits the home position, step 630.

As stated above, different position devices such as encoders, absolute position encoders etc may be used. Therefore, some steps of the invented method has to be modified.

The present invention may be implemented as a computer program product directly loadable into an internal memory storage of a processing unit within the controller in the microfluidic system, comprising the software code means for performing the steps of any of claims 1-9.

Further, the present invention relates to a computer program product stored on a computer usable medium, comprising readable program for causing a processing unit in a computer means to control an execution of the steps of any of the claims 1-9.

The computer usable medium is a record medium, a computer memory, a Read-Only Memory or an electrical carrier signal The present invention is not limited to the above-described preferred embodiments. Various alternatives, modifications and equivalents may be used. Therefore, the above embodiments should not be taken as limiting the scope of the invention, which is defined by the appended claims.

The invention claimed is:

1. A method for determining the identity of a microfluidic disc and a home position on said microfluidic disc, said microfluidic disc having a plurality of home position marks thereon, wherein said microfluidic disc is of the type used in a microfluidic system comprising at least one programmable controller having storage means, a position device being able to communicate with the controller, and a home position mark detector in communication with said controller, said method comprises following steps:

scanning said microfluidic disc for home position mark identifiers;

identifying said microfluidic disc said step of identifying comprises determining at least one characteristic feature of said plurality of home position marks; and, determining said home position, wherein said step of determining comprises using at least a subset of said plurality of home position marks identified during said steps of scanning and identifying.

2. The method of claim 1, wherein the method further comprises the steps of:

scanning and detecting mark identifiers on said microfluidic disc by rotating the disc in a first direction a predetermined scanning distance from an arbitrary start position on said microfluidic disc said step of scanning and detecting performed by a home mark detector means;

storing in a storage means one or more position values for said mark identifiers corresponding to a plurality of home position marks;

stopping said scanning and detecting of the microfluidic disc in said first direction, said step of stopping being performed when the microfluidic disc has rotated a predetermined scanning distance from said arbitrary start position;

scanning said microfluidic disc by rotating it in a second direction, said second direction opposite from said first direction; and, determining said home position by means of at least two positions from said plurality of home position marks.

3. The method according to claim 1, wherein said step of identifying further comprises:

arranging position values of mark identifiers in a series according to scanned positions acquired during a previous scanning phase.

4. The method according to claim 3, wherein said disc of identifying further comprises:

calculating angular lengths and/or distances between adjacent position values and arranging said lengths and/or distances in a calculated length series S.

5. The method according to claim 4, wherein said step of identifying further comprises:

comparing said series S, element by element, to a series, S*n, said series, S*n, being pre-stored in a home position mark identification table.

6. The method according to claim 5, wherein said step of identifying further comprises the following steps:

if a match S=S*n is detected, identifying said microfluidic disc and determining said home position; and, reading data pertaining to said microfluidic disc in said home position mark identification table and displaying results on an operator display screen or other display device.

7. The method according to claim 5, wherein said step of identifying further comprises the following steps:

if no match S=S*n is detected, performing an order checking phase comprising the step of determining if marks comprising said plurality of home position marks are scanned in the correct order when scanned in a predetermined positive direction.

8. The method according to claim 7, characterised in that, further comprising:

if no match S=S*n is detected, generating an error code or message and displaying the error code or message on an operator display screen or other display device.

9. The method according to claim 7, wherein said step of determining the home position comprises the use of position values of said plurality of home position marks, wherein said home position marks are defined anywhere on or between two position values of any of said home position marks.

10. A computer program product comprising:
a non-transitory computer usable medium carrying computer program software code loadable into an internal memory storage of a processing unit within a computer means, said computer means comprising a controller of a microfluidic system; and,
software code for performing a method for determining the identity of a microfluidic disc and a home position on said microfluidic disc by means of a plurality of home position marks on said microfluidic disc wherein said microfluidic disc is of the type used in a microfluidic systems comprising at least one programmable controller having storage means, a position device being able to communicate with the controller, and a home position mark detector connected to said controller, wherein said method comprises following steps:
scanning said microfluidic disc for home position mark identifiers;
identifying said microfluidic disc said step of identifying comprises determining at least one characteristic feature of said plurality of home position marks; and,
determining said home position, wherein said step of determining comprises using at least a subset of said plurality of home position marks identified during said steps of scanning and identifying.

11. The computer program of claim 10, wherein the method further comprises the steps of:
scanning and detecting mark identifiers on said microfluidic disc by rotating the disc in a first direction a predetermined scanning distance from an arbitrary start position on said microfluidic disc said step of scanning and detecting performed by a home mark detector means;
storing in a storage means one or more position values for said mark identifiers corresponding to said plurality of home position marks;
stopping said scanning and detecting of the microfluidic disc in said first direction, said step of stopping being performed when the microfluidic disc has rotated a predetermined scanning distance from said arbitrary start position;
scanning said microfluidic disc by rotating it in a second, direction, said second direction opposite from said first direction; and,
determining said home position by means of at least two positions from said plurality of home position marks.

12. The computer program of claim 10, wherein said computer program is stored on a computer usable medium, comprising a readable program for a processing unit in said computer means.

13. The computer program according to claim 10, wherein the computer usable medium is selected from the group consisting of a record medium, a computer memory, a Read-Only Memory, and an electrical carrier signal.

14. A microfluidic system comprising:
at least one microfluidic instrument;
a programmable controller having storage means, said programmable controller control of said at least one microfluidic instrument;
a position device in communication with said controller,
a home position mark detector in communication with said controller,
wherein said microfluidic instrument comprises one or more microfluidic disc having a plurality of home position marks thereon, and,
a computer program loadable into an internal memory storage of a processing unit within said controller, said computer program operable to instruct said controller to perform a method, said method for determining the identity of said microfluidic disc via a home position on said microfluidic disc by means of a plurality of home position marks on said microfluidic disc wherein said microfluidic disc is of the type used in a microfluidic systems comprising at least one programmable controller having storage means, a position device being able to communicate with the controller, and a home position mark detector connected to said controller, wherein said computer program comprises instructions directing the following steps:
scanning said microfluidic disc for home position mark identifiers; identifying said microfluidic disc said step of identifying comprises determining at least one characteristic feature of said plurality of home position marks; and,
determining said home position, wherein said step of determining comprises using at least a subset of said plurality of home position marks identified during said steps of scanning and identifying.

15. The microfluidic system of claim 14, wherein said computer
program further comprises instructions directing the following steps:
scanning and detecting mark identifiers on said microfluidic disc by rotating the disc in a first direction a predetermined scanning distance from an arbitrary start position on said microfluidic disc said step of scanning and detecting performed by a home mark detector means;
storing in a storage means one or more position values for said mark identifiers corresponding to a plurality of home position marks;
stopping said scanning and detecting of the microfluidic disc in said first direction, said step of stopping being performed when the microfluidic disc has rotated a predetermined scanning distance from said arbitrary start position;
scanning said microfluidic disc by rotating it in a second direction, said second direction opposite from said first direction; and, determining said home position by means of at least two positions from said plurality of home position marks.

16. The microfluidic system of claim 14, wherein the home position mark detector comprises means to detect a home position mark of a microfluidic device disc type.

17. The microfluidic system of claim 16, wherein that the home position mark detector comprises an electromagnetic beam source and a transducer arrangement.

18. The microfluidic system of claim 14, wherein the controller comprises a position controlling means to receive or transmit different data using a position signal.

19. The microfluidic system of claim 18, wherein the position device is an encoder generating a pulse for each resolution grade and the position controlling means comprises a pulse counter for registering a pulse sum value representing a current position of the disc relative to a start position or the home position and the detector.

20. The microfluidic system of claim 18, wherein the position device is an absolute encoder, and the position controlling means comprises means to receive or transmit an absolute measure of an angular distance from a start position or the home position.

21. A microfluidic disc comprising a plurality of home position marks wherein said plurality of home position marks comprises at least two home position marks defining one or more detectable characteristic features of said disc.

22. The microfluidic disc of claim 21, wherein the characteristic features are the angular length and/or distance between home position marks.

23. The microfluidic-disc of claim 21, wherein one of said home position marks is a leading home position mark which has a unique detectable feature distinguishing the leading home position mark from the other marks of the plurality, and wherein one other of said home position marks of said plurality is a trailing home position mark which has a unique detectable feature distinguishing the trailing home position mark from the other marks of the plurality.

24. The microfluidic-disc of claim 23, wherein the leading mark has a detectable leading identifier and a detectable trailing identifier, and the trailing mark has a detectable leading identifier and a detectable trailing identifier, and the exact home position is situated in an area defined from the position of leading identifier of the leading mark to the position of the trailing identifier of the trailing mark, the positions of said identifiers incorporated in said area.

25. The microfluidic-disc of claim 24, wherein said identifiers are detectable home position mark edges.

26. The microfluidic disc of claim 23, wherein the leading mark has a detectable leading identifier and a detectable trailing identifier, and the trailing mark has a detectable leading identifier and a detectable trailing identifier, and the exact home position is situated somewhere outside the area defined from the position of leading identifier of the leading mark to the position of the trailing identifier of the trailing mark, the positions of said identifiers incorporated in said area.

27. The microfluidic disc of claim 23, wherein a home position mark, having a detectable leading identifier and a detectable trailing identifier, is situated between the leading mark and the trailing mark, the home position being situated in the area between the position of the leading identifier of the home position mark and the position of the trailing identifier of the home position mark, the positions of said identifiers incorporated in said area.

28. The microfluidic disc of claim 21, comprising at least one microchannel area having one or more microchannel structures.

29. The microfluidic disc of claim 28, wherein the microfluidic i:hwi-t::-t'-dtsc carries at least one set of home marks in an outer circumferential zone outside the detection area comprising microchannel structures.

30. The microfluidic disc of claim 28, wherein the microfluidic disc carries at least one set of home marks in the detection area comprising microchannel structures.

* * * * *

UNITED STATES PATENT AND TRADEMARK OFFICE
CERTIFICATE OF CORRECTION

| | | |
|---|---|---|
| PATENT NO. | : 8,600,684 B2 | Page 1 of 1 |
| APPLICATION NO. | : 11/916012 | |
| DATED | : December 3, 2013 | |
| INVENTOR(S) | : Ohlstrom et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1360 days.

Signed and Sealed this
Twenty-first Day of July, 2015

Michelle K. Lee
*Director of the United States Patent and Trademark Office*